United States Patent [19]

Tornier

[11] Patent Number: 4,483,335

[45] Date of Patent: Nov. 20, 1984

[54] NAILS FOR FEMORAL FRACTURES

[75] Inventor: Alain Tornier, Crolles, France

[73] Assignee: Tornier S.A., Saint Ismier, France

[21] Appl. No.: 500,646

[22] Filed: Jun. 2, 1983

[30] Foreign Application Priority Data

Jun. 2, 1982 [FR] France .................. 82 09838

[51] Int. Cl.³ .............................. A61F 5/04
[52] U.S. Cl. .................. 128/92 BC; 128/92 BA
[58] Field of Search ............ 128/92 R, 92 B, 92 BA, 128/92 BC, 92 D

[56] References Cited

U.S. PATENT DOCUMENTS

| 4,055,172 | 10/1977 | Ender et al. | 128/92 BC |
| 4,135,507 | 1/1979 | Harris | 128/92 BC |
| 4,169,470 | 10/1979 | Ender et al. | 128/92 BC |

Primary Examiner—C. Fred Rosenbaum
Assistant Examiner—C. W. Shedd
Attorney, Agent, or Firm—Dowell & Dowell

[57] ABSTRACT

A nail for the osteosynthesis of fractures of femoral necks, formed of a resilient pre-curved rod having an inner end engageable into the medullary cavity of the femur through a lateral perforation drilled through the inner side of said femur in the vicinity of the process thereof and an outer end which remains exterior to said femur. The rod comprises in the vicinity of said outer end a portion which is bent twice in opposed directions to determine a shoulder which protrudes inwardly with respect to the curvature of said rod and which abuts against the edge of said perforation to retain said nail longitudinally with respect to said femur.

3 Claims, 2 Drawing Figures

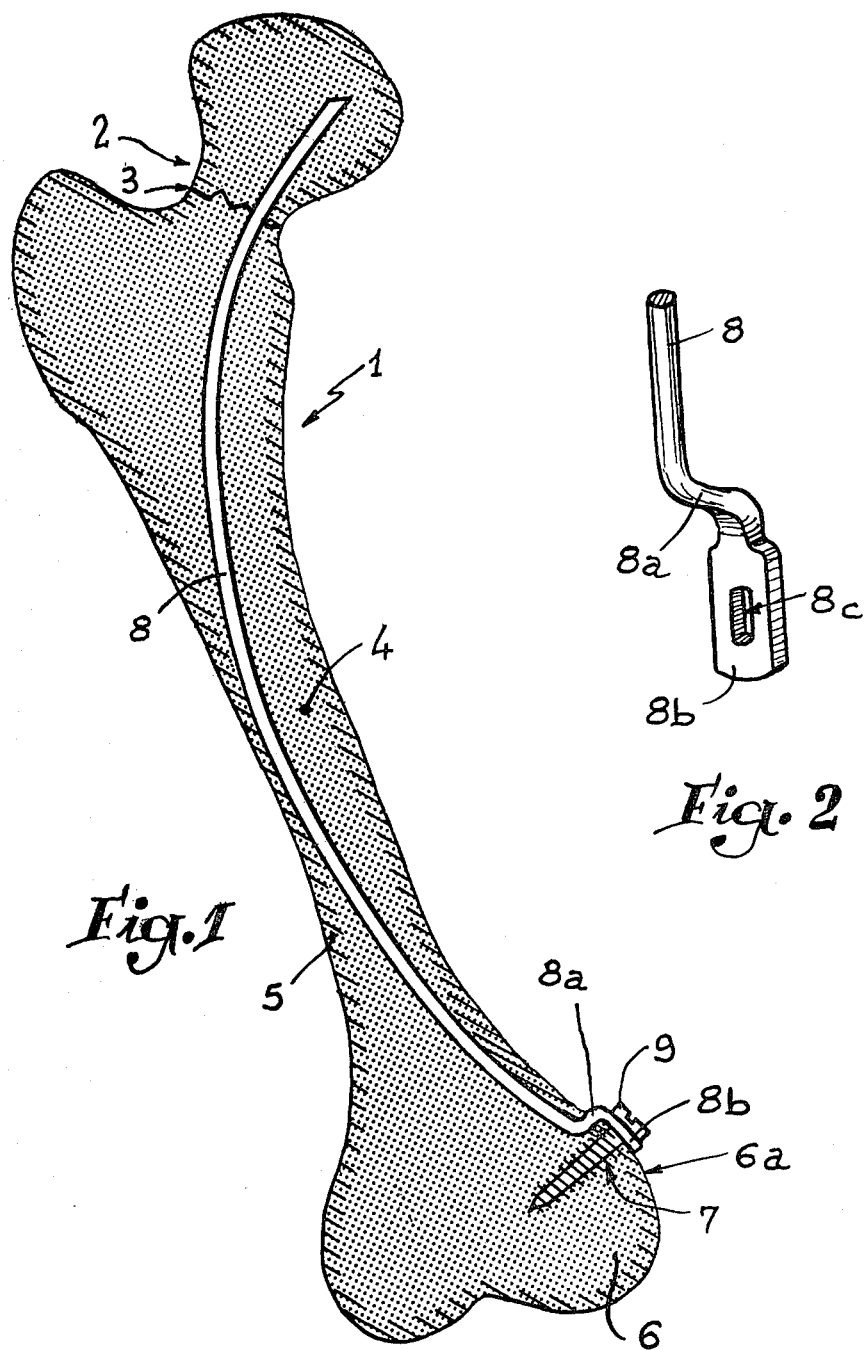

NAILS FOR FEMORAL FRACTURES

The present invention relates to improvements in prostheses and more particularly to the rods or nails for the osteosynthesis of the fractures of the neck of the femur.

In a known mode of osteosynthesis of such fractures a pre-curved rod or nail of small diameter is engaged into the medullary cavity of the femur in such a manner that its end portion becomes placed in the fractured zone.

Owing to the relative flexibility of such a nail, three of them are generally used for the same fracture so as to realize a sufficiently rigid armature.

The main drawback of this method is that the nails thus disposed have a marked tendency to slip backwards through their inlet hole. When this occurs the fractured portion of the femur is no more appropriately supported.

It is an object of the present invention to avoid this drawback.

For this purpose the end of each nail opposed to the portion which is driven into the fractured zone of the femur is bent twice in opposed directions so as to form a shoulder which is used as an abutment resting against the wall of the perforation through which than nail has been engaged into the medullary cavity of the femur, thus preventing any backward movement of the nail with respect to the bone.

In order to more surely retain the nail in position, its outer end may be provided with a flat perforated portion which may be fixed to the bone by means of a screw.

In the accompanying drawings:

FIG. 1 is a diagrammatical section of a fractured femur, illustrating how a nail according to the invention is disposed in the meddulary cavity.

FIG. 2 is an enlarged perspective view showing the outer end to the nail searately of the femur itself.

In FIG. 1 a femur 1 is fractured in the zone of its neck 2 as illustrated by the broken line 3. The medullary cavity of femur 1 is designated by reference numeral 4. It is supposed that the patient is relatively aged. Therefore the bone comprises almost no sponge-like substance, but only a cortex 5 of small thickness.

After the reduction of the fracture, the surgeon perforates in the process or apophysis 6 of the femur 1 a hole 7 which, starting from the inner side 6a of the process, opens into the medullary cavity 4. After this prelinary operation he engages one or more nails 8 into the medullary cavity as this is well known in the art.

But in accordance with the invention the outer end of the nail or nails is bent twice in opposed directions, as illustrated in FIG. 2, in such manner as to form a shoulder 8a substantially perpendicular to the preceding portion of the nail, and thereafter a terminal portion 8b parallel to the said preceding portion. Portion 8b is flattened in the form of a plate and it is drilled as indicated at 8c.

Of course during its introduction into the medullary cavity the nail 8 is submitted to resilient deformations since its shape in the free state does not exactly correspond to that of the said cavity. Under these conditions and due to the material from which it is made, each nail is noticeably deformed, more particularly in the zones of the neck 3 and of the lower process 6. Owing to these resilient deformations the two portions of the neck 2 are maintained in position with respect to each other after the reduction of the fracture. As to the deformation in the lower zone of hole 7, it has for its result that the shoulder 8a is efficiently maintained in the said hole and is therefore retained against any relative displacement with respect to the cortex 5. The flattened portion or plate 8b, which remains exterior to the bone, may be fixed to the inner side of the process by means of a screw 9, if required.

There has thus been realized in accordance with the invention a nail for the osteosynthesis of the fractures of femoral necks, which if positively retained in position as long as this may be considered as necessary for the re-calcification, even independently of screw 9 which is only provided as a matter of additional safety.

What is claimed is:

1. In a nail for the osteosynthesis of fractures of femoral necks, formed of a resilient pre-curved rod having an inner end engageable into the medullary cavity of the femur through a lateral perforation drilled through the inner side of said femur in the vicinity of the process thereof and an outer end which remains exterior to said femur, with said perforation having an edge, said rod comprising in the vicinity of said outer end a portion which is bent twice in opposed directions to determine a shoulder which protrudes inwardly with respect to the curvature of said rod and which abuts against the edge of said perforation to retain said nail longitudinally with respect to said femur.

2. In a nail as claimed in claim 1, said outer end terminating in a flattened portion which rests against the exterior of said process.

3. In nail as claimed in claim 2, said flat portion having a hole for passage of a screw adapted to fix said flattened portion to said femur.

* * * * *